(12) United States Patent
Richards et al.

(10) Patent No.: US 7,634,157 B1
(45) Date of Patent: Dec. 15, 2009

(54) INFRARED AND NEAR-INFRARED CAMERA HYPERFRAMING

(75) Inventors: Austin A. Richards, Santa Barbara, CA (US); Shariff D'Souza, Santa Barbara, CA (US)

(73) Assignee: FLIR Systems, Inc., Wilsonville, OR (US)

( * ) Notice: Subject to any disclaimer, the term of this patent is extended or adjusted under 35 U.S.C. 154(b) by 684 days.

(21) Appl. No.: 11/388,947

(22) Filed: Mar. 23, 2006

(51) Int. Cl.
*G06K 9/54* (2006.01)
*G06K 9/36* (2006.01)

(52) U.S. Cl. .................................. 382/305; 382/284

(58) Field of Classification Search ................. 382/305, 382/284, 167, 209; 348/221.1, 218.1; 396/322–353, 396/18, 265; 359/629–634, 353, 485, 493–501; 250/333, 343, 347; 356/3.01, 4.01, 300, 356/139.01–139.1; 436/164, 171–172, 159, 436/147
See application file for complete search history.

(56) References Cited

U.S. PATENT DOCUMENTS

| | | | |
|---|---|---|---|
| 6,370,338 B1 | 4/2002 | Chan | |
| 6,639,625 B1 | 10/2003 | Ishida et al. | |
| 6,849,460 B2 * | 2/2005 | McFarland et al. | 436/171 |
| 7,158,323 B2 | 1/2007 | Kim et al. | |
| 7,307,793 B2 | 12/2007 | Ottney et al. | |
| 7,450,839 B2 | 11/2008 | Lee et al. | |
| 7,528,938 B2 * | 5/2009 | Garceau et al. | 356/4.01 |
| 2004/0081451 A1 | 4/2004 | Takada | |
| 2008/0252882 A1 | 10/2008 | Kesterson | |

OTHER PUBLICATIONS

"Multispectral Imaging IR Camera", CEDIP Infrared Systems brochure, 2004 (pp. 1-2).
Austin Richards, "Extending IR camera scene radiance dynamic range with cyclic integration times", Proceedings of SPIE, vol. 5782, Thermosense XXVII, Mar. 2005 (pp. 93-99).
U.S. Appl. No. 11/388,711, Richards et al.
Meitzler et al., Multiband Imagery for Concealed Weapon Detection (U), U.S. Army TACOM, Survivability Technology Area, pp. 1-7.
Robinzon et al., "Infrared Scene Generator for a Flight Motion Simulator", SPIE vol. 2020 Infrared Technology XIX (1993), pp. 150-160.
Preston et al., Development of a Field-Portable Multispectral Imaging and Classification System, ASPRS/ACSM (1994).

* cited by examiner

*Primary Examiner*—Sherali Ishrat
(74) *Attorney, Agent, or Firm*—Haynes and Boone, LLP

(57) ABSTRACT

Systems and techniques for imaging spectroscopy using improved data acquisition for infrared and near-infrared imaging. A first filter corresponding to a first wavelength may be positioned in the optical path of an infrared camera, and subframe data may be acquired for different exposures. A second filter corresponding to a second different wavelength may be positioned in the optical path of the infrared camera, and subframe data acquired for different exposures. Image data for the first wavelength and the second wavelength may then be compared to reference spectroscopic data.

20 Claims, 7 Drawing Sheets

INFRARED AND NEAR-INFRARED CAMERA HYPERFRAMING

BACKGROUND

1. Field of Invention

This invention generally relates to infrared (and near-infrared) cameras and, more particularly, to enhanced dynamic-range cameras.

2. Related Art

Infrared cameras may be used to image objects and scenes by detecting radiation in the thermal infrared and/or near-infrared range. In general, the characteristics of this radiation are dependent (in part) on the temperature of the radiating object.

Infrared cameras use detectors to image objects of interest, as single images or video. One type of infrared detection system is a focal plane array (FPA). An FPA system uses an array of infrared detectors such as photodiodes or bolometers, where the output of each detector in the array is used as intensity information for an associated image pixel. Different types of detectors are sensitive to different wavelength ranges.

For some objects or scenes, there may be a wide range of in-band brightness in the field of view of interest. For example, a rocket launch scene may include both a cold rocket hardbody and an extremely hot exhaust plume. Since a typical IR camera has a brightness dynamic range of about 12-14 bits, it may be impossible to fully span such a scene with a single exposure value. The brightest or hottest parts of the image will often be saturated, while the darkest or coolest part of the scene may appear black in the image (since the signal is buried in the noise floor of the camera).

Additionally, in some circumstances the dynamic range of a scene at a particular time may not be large, but may change substantially in a short amount of time (for example, a rocket launch scene at a time just prior to launch versus a time just after launch commences). Although a single exposure value may be appropriate to image the entire scene at a particular time, if the temperature profile changes substantially, the exposure may not provide for acquisition of adequate image data at a later time.

For a particular IR camera and expected brightness range, imaging may be optimized by adjusting the camera to an optimal shutter speed or integration time. However, it may not be possible to fully encompass a scene's brightness (temperature) variations using a single integration time.

SUMMARY

Systems and techniques for imaging spectroscopy using improved dynamic range detection of IR and near-IR from one or more targets.

In general, in one aspect, an article comprises a machine-readable medium embodying information indicative of instructions that when performed by one or more machines result in operations comprising positioning a first filter in the optical path of an infrared camera, the first filter configured to pass a narrow wavelength band including a first wavelength, acquiring first subframe image data associated with the first wavelength at a detector using a first exposure, acquiring second subframe image data associated with the first wavelength at the detector using the second exposure, and generating first wavelength image data based on at least some of the first subframe image data and the second subframe image data. The operations may further comprise positioning a second filter in the optical path of the infrared camera, the second filter configured to pass a narrow wavelength band including a second different wavelength, acquiring image data associated with the second wavelength at the detector, and generating second wavelength image data based on the image data associated with the second wavelength. The operations may further comprise comparing the first wavelength image data and the second wavelength image data to reference spectroscopic data.

The operations may further comprise determining the presence or absence of a particular material corresponding to the reference spectroscopic data. The first wavelength image data may comprise image data corresponding to a plurality of pixels of the image, and comparing the first wavelength image data to reference spectroscopic data may comprise comparing first wavelength data for each of the plurality of pixels to the reference spectroscopic data.

Acquiring the first subframe image data associated with the first wavelength at the detector using the first exposure may comprise acquiring the first subframe image data at a first integration time, and acquiring the second subframe image data associated with the first wavelength at the detector using the second exposure may comprise acquiring the first subframe image data at a second different integration time.

Acquiring the first subframe image data associated with the first wavelength at the detector using the first exposure may comprise acquiring the first subframe image data using a first filter with a first attenuation, and acquiring the second subframe image data associated with the first wavelength at the detector using the second exposure may comprise acquiring the first subframe image data using a second filter with a second different attenuation.

Comparing the first wavelength image data and the second wavelength image data to reference spectroscopic data may comprise comparing the first wavelength image data and the second wavelength image data to reference spectroscopic data corresponding to a plurality of different materials. The first wavelength image data may comprise image data corresponding to a plurality of pixels of the image, and comparing the first wavelength image data to reference spectroscopic data corresponding to the plurality of different materials may comprise comparing first wavelength data for each of the plurality of pixels to the reference spectroscopic data for at least one of the different materials.

In general, in another aspect, a method may include positioning a first filter in the optical path of an infrared camera, the first filter configured to pass a narrow wavelength band including a first wavelength, acquiring first subframe image data associated with the first wavelength at a detector using a first exposure, acquiring second subframe image data associated with the first wavelength at the detector using the second exposure, and generating first wavelength image data based on at least some of the first subframe image data and the second subframe image data. The method may further include positioning a second filter in the optical path of the infrared camera, the second filter configured to pass a narrow wavelength band including a second different wavelength, acquiring image data associated with the second wavelength at the detector, and generating second wavelength image data based on the image data associated with the second wavelength. The method may further comprise comparing the first wavelength image data and the second wavelength image data to reference spectroscopic data.

In general, in another aspect, an infrared camera system may comprise a filter holder configured to hold a first spike filter associated with a first wavelength and a second spike filter associated with a second wavelength, the filter holder further configured to position the first spike filter in the optical path of the infrared camera system for a first time interval and to position the second spike filter in the optical path of the infrared camera system for a second time interval.

The system may further comprise a detection system configured to receive light from the first spike filter at a first exposure and to generate first subframe information indicative thereof. The detection system may further be configured to receive light from the first spike filter at a second exposure and to generate second subframe information indicative thereof. The detection system may further be configured to receive light from the second spike filter at the first exposure and to generate third subframe information indicative thereof. The detection system may further be configured to receive light from the second spike filter at the second exposure and to generate fourth subframe information indicative thereof.

The system may further comprise a processor configured to receive the first subframe information and the second subframe information and to generate first superframe information associated with the first wavelength based on at least a part of the first subframe information and the second subframe information. The processor may further be configured to receive the third subframe information and the fourth subframe information and to generate second superframe information associated with the second wavelength based on at least a part of the third subframe information and the fourth subframe information. The processor may further be configured to compare the first superframe information and the second superframe information to reference spectroscopic data. The infrared camera may comprise a near-infrared (NIR) camera.

These and other features and advantages of the present invention will be more readily apparent from the detailed description of the exemplary implementations set forth below taken in conjunction with the accompanying drawings.

BRIEF DESCRIPTION OF THE DRAWINGS

Like reference symbols in the various drawings indicate like elements.

DETAILED DESCRIPTION

Systems and techniques provided herein may allow for enhanced dynamic range capability in thermal IR and near-IR imaging. For simplification, the term "IR" herein encompasses both IR and near-IR spectral ranges, while the term "near-IR" refers particularly to the near-IR part of the spectrum, ranging in wavelength from about 900 to about 1700 nm.

One technique that may be used to increase the dynamic range of an IR imaging system is electronic superframing. Superframing refers to a process by which image data for a plurality of images (subframes) is combined to generate a single image with enhanced dynamic range. Each of the subframes has a different exposure, which may be controlled (for example) by changing the shutter speed and/or integration time of the imaging system.

The superframing technique is particularly useful for infrared camera systems that are used to image scenes with large difference in temperature, such as the rocket launch described above. With prior techniques, in order to obtain an image of the cold hardbody surface, the sensitivity of the camera would initially have to be set to high to properly image the thermal features of the cold hardbody surface. However, at an exposure where thermal features of the cold hardbody can be distinguished, the brightness of the exhaust plume generated at ignition rapidly saturates the detection elements of the camera.

One technique that may be used for rocket launch imaging is that, just after ignition, the sensitivity of the camera may be substantially reduced. For example, an integration time of several milliseconds may be used to image the hardbody prior to ignition, then the integration time may be reduced to about 10 microseconds (for an exemplary indium antimonide (InSb) camera with a 3 to 5 micron bandpass). Although this allows the thermal profile of the plume to be imaged, the decreased sensitivity prevents contemporaneous thermal imaging of the much colder hardbody.

Some existing systems use multiple IR cameras set to various integration times on the scene of interest, in order to obtain image data for a wider thermal range. However, this solution is complex and introduces errors (such as error due to parallax).

By contrast, superframing provides a relatively simple and accurate technique to perform IR imaging of scenes with large thermal differences. Superframing may be accomplished using electronic techniques, mechanical techniques, or a combination.

Figure 1A:
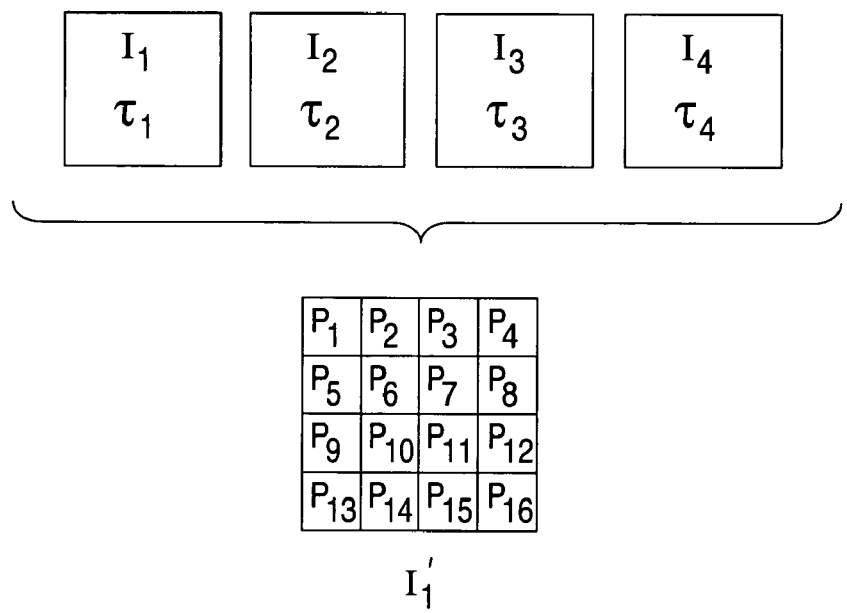
FIG. 1A shows four subframes and an associated superframe that may be generated using electronic superframing.
Figure 1B:
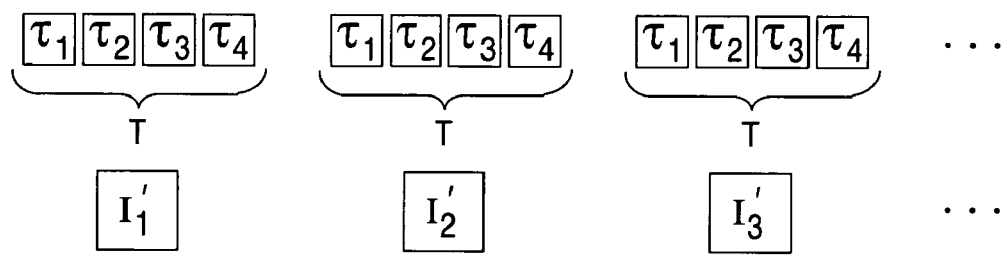
FIG. 1B shows a series of subframes and associated superframes that may be generated using electronic superframing.

FIG. 1A illustrates an existing electronic superframing technique. An IR camera is configured to acquire a first series of images $I_1$, $I_2$, $I_3$, and $I_4$, which are referred to as "subframes." Each of the subframes is acquired at a different exposure value. In the example shown in FIG. 1, each of the subframe images $I_1$, $I_2$, $I_3$, and $I_4$ are acquired using different exposures, by varying the integration time $\tau$. A set of four subframes is acquired in a total time T.

If T is small compared to the time over which the scene changes, a dataset for images $I_1$, $I_2$, $I_3$, and $I_4$ may be reduced to provide data for a "superframe," shown as image $I_1'$ of FIG. 1A. For a subframe rate $R_1$ of 100 frames per second, and four subframes per superframe (as shown), $R_2$ (the frame rate with subframe cycling, which is also equal to 1/T) is 25 frames per second.

Each of the subframes and the superframe include image data for an array of pixels. For example, image $I_1'$ includes sixteen image pixels $P_1$ to $P_{16}$, each of which corresponds to one of sixteen pixels in each of the subframes $I_1$, $I_2$, $I_3$, and $I_4$ (not shown). The image information for the subframe pixels is used to generate image information for each of the superframe image pixels $P_1$ to $P_{16}$. For example, image information for a particular superframe image pixel may be derived from image information for the corresponding pixel in the one of the subframes that provides the longest integration time (and therefore, highest sensitivity) without exceeding a saturation threshold.

For example, if the portion of the scene being imaged corresponding to pixel $P_1$ is a relatively cool portion of the object to be imaged, image data for pixel $P_1$ of superframe $I_1'$ may be generated using the corresponding image data for the subframe with the longest exposure time. For other pixels of superframe $I_1'$, corresponding image data from one or more of the other subframes may be used to generate image data for the superframe pixel.

An exemplary application of electronic superframing is as follows. An IR camera such as an InSb camera may be configured to cycle through four integration times in succession (as in FIG. 1A). Because dark current values for each pixel generally change with integration time, each integration time may have an associated non-uniformity correction (NUC). The NUCs are referred to as presets, and for the example described herein are typically numbered between 0 and 3.

The integration times for each preset may be chosen based on a geometric progression between the desired endpoint integration times. By selecting the integration times in this manner, the generated exposures will have plenty of overlap in the radiance ranges that can be accommodated, while maintaining a substantially linear response. The desired endpoint integration times may be selected based on the expected properties of the scene to be imaged (e.g., the thermal range of the scene to be imaged) and/or system constraints.

For example, for an f/2.5 coldshield and 90% transmitting optics, a typical InSb camera images scene temperatures between −20° C. and 50° C. at about 2000 microseconds integration time (assuming unity emissivity for simplicity). Each of the pixels of the camera may be thought of as "buckets," with a capacity of about $1.8 \times 10^7$ electrons. After 2000 μsec, a 50° C. target will fill the bucket to the point where its response is starting to be non-linear. With an integration time of 30 microseconds, the temperature range that can be imaged is between about 90° C. and 300° C.

The interval between the limits of 2000 microseconds and 30 microseconds corresponds to a factor of 66.7. To select additional integration times based on geometric progression, the geometric steps are obtained by dividing the integration times in steps of the cube root of 66.7, which is about 4. For the current example, the selected integration times for the four presets are shown in Table 1 below.

TABLE 1

| Pre-set Number | Integration Time (microseconds) |
|---|---|
| 0 | 2000 |
| 1 | 500 |
| 2 | 125 |
| 3 | 30 |

To obtain data for a single superframe, data for a series of four subframes having the above integration times is obtained. A dataset taken with a camera configured to implement superframing techniques thus consists of four-image cycles of images that can be post-processed down to generate a sequence of superframes.

Post-processing may be accomplished in a number of ways. For example, image data corresponding to a particular pixel of a superframe may be the image data corresponding to the subframe having the best image quality for that pixel. For the current example, the best image quality pixel is the pixel associated with the subframe having the highest integration time without exceeding a saturation threshold. The saturation threshold may be the digital count value for which the detector is still in a linear regime (typically 80% of full scale, or about 12,000 counts for a 14-bit camera, which has a digitizer range from 0 to 16383 digital counts).

Figure 2:
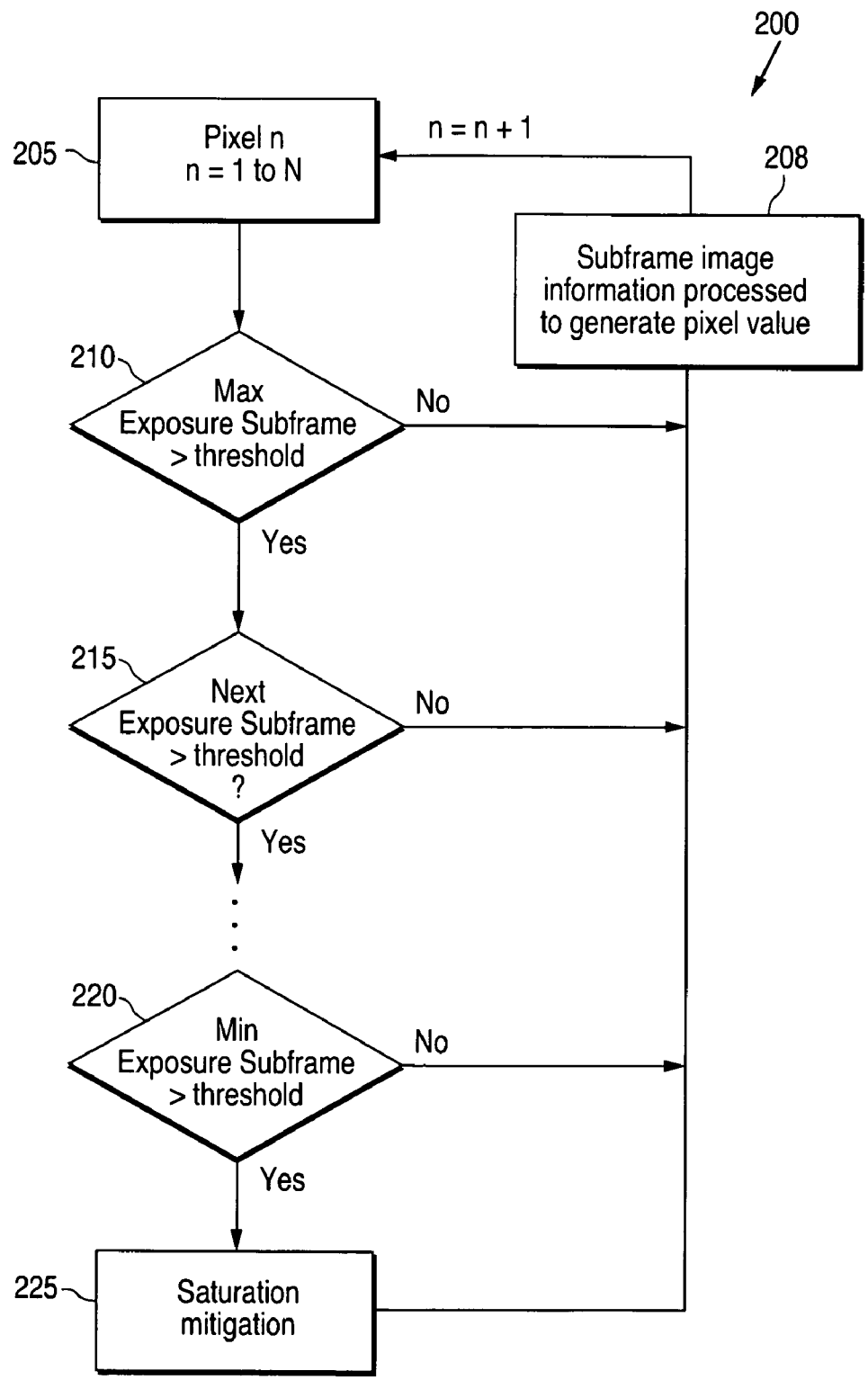
FIG. 2 is a method that may be used to generate N pixels for a superframe using image data for a plurality of subframes.

To generate image data for the superframe, software and/or hardware may implement a method 200 such as that shown in FIG. 2. At 205, an nth pixel of N total pixels may be selected. For example, the first (n=1) pixel may be the pixel in the corner of the FPA, which may have a coordinate value defined as (0, 0). For the nth pixel, the value for the subframe having the maximum exposure (here, the 2000 microsecond preset) is compared to a threshold at 210. If the value of the subframe pixel does not exceed the threshold, that value may then be processed at 208 to generate image data for the nth pixel of the superframe. Image information for the next superframe pixel (e.g., the n=2 pixel) may then be determined in a similar manner.

At 215, if the pixel value for the subframe having the maximum exposure exceeds the threshold, the value of the nth pixel for the subframe having the next lower exposure is compared to the threshold (in this example, the 500 microsecond preset). If the value of the subframe pixel does not exceed the threshold, the value may then be processed at 208 to generate image data for the nth pixel of the superframe.

The process continues until the pixel value for the subframe corresponding to the minimum exposure is compared to the threshold at 220. If the pixel value does not exceed the threshold, the value may be processed at 208 to generate image data for the nth pixel of the superframe. If the pixel value for the subframe corresponding to the minimum exposure exceeds the threshold, one or more saturation mitigation techniques may optionally be implemented at 225, or the saturated pixel value may be used to generate image data for the nth pixel of the superframe.

A number of different saturation mitigation techniques may be used. For example, for pixel values that exceed the threshold but are less than full scale, the pixel values may be corrected using a saturation algorithm (e.g., a non-linear correction may be made to the pixel value based on pre-characterization of the saturated sensors). In another example, pixel data for one or more neighboring pixels may be used to generate a value for the nth pixel of the superframe (e.g., using interpolating techniques).

As noted above, pixel values for the subframes may be processed at 208 to generate image data for the superframe pixels. For example, the pixel values may be converted from counts to engineering radiance units, typically Watts/(cm$^2$-sr). The resulting radiometric units may be correlated with the radiant energy emitted by the target of interest; for example, using the following calibration process.

The camera may be exposed to a calibration target of known radiance (e.g., a temperature-controlled blackbody), and the camera response recorded (e.g., the number of counts recorded for each of the pixels). The source radiance is then varied, new measurements taken, and calibration information (e.g., a calibration table) is generated. Because IR cameras are generally designed to produce a digital output signal that is very linear in the flux reaching the FPA, a linear expression may be fit to the calibration table and the resulting calibration applied to pixel count values.

The radiometric calibration described above results in a transfer function between the digital counts (the output of the camera) and the apparent radiance of the target (in radiometric units). This is generally a simple linear function that may be represented by two coefficients: the slope and intercept of the linear fit. The coefficients change in inverse proportion to integration time, where the shorter the integration time, the higher the radiance of a given pixel count value.

The above-described electronic superframing techniques may provide a number of benefits over other existing IR imaging techniques. Image dynamic range is increased, but without sacrificing noise performance, since each pixel in the resulting superframe is selected from the subframe with the lowest NEI (Noise-equivalent Irradiance) or NEdT (Noise Equivalent Difference of Temperature) while remaining within the linear portion of the dynamic range of the ROIC (Readout Integrated Circuit). NEI may be used for near-IR cameras, rather than NEdT, although other embodiments are possible.

However, electronic superframing may not be optimal in some circumstances. For example, in IR camera systems incorporating FPAs, externally-generated bias signals are generally provided from off-chip. In order to provide a wide range of integration times, the bias levels need to be adjusted. However, because the bias signals generally have settling times greater than typical sub-frame periods, bias signal adjustment is not practical for a cyclical superframe implementation. Therefore, in practice, the range of integration times that may be used are those that may be obtained with a single set of bias settings. For example, in some systems, the integration time may only be varied by a factor of about 100.

Another challenge with electronic superframing is that the maximum frame rate is limited by the longest integration time in the cycle. For example, for a system configured to run with three presets corresponding to integration times of 10 msec, 1 msec, and 0.1 msec, the maximum frame rate is less than 100 Hz (limited by the 10 msec integration time). For spatially dynamic scenes, subframe image data obtained with longer integration times may be blurred relative to shorter integration times.

Accordingly, systems and techniques herein provide for improved imaging using mechanical superframing instead of (or in addition to) electronic superframing. In mechanical superframing, a plurality of optical elements are positioned in the optical path in turn, so that each of a set of subframes is acquired with a different exposure. For example, each of a plurality of filters (such as neutral density filters, bandwidth filters, spike filters and/or other filters) may be positioned in turn between the lens and detector array of an IR camera.

Mechanical superframing may be particularly well-suited to imaging in the near-IR (NIR) spectrum. NIR imaging is important for a number of applications. One important application is the imaging of objects through atmosphere, where visible-light images may be unduly distorted by interaction of optical photons with atmospheric constituents. Some subbands of NIR (e.g., NIR with wavelengths of about 1.2 microns) travels through the atmosphere relatively unaffected, and may thus provide more accurate images.

NIR imaging is also an important technique for understanding the physical properties of materials as a function of temperature, since in-band radiance in the NIR region of the electromagnetic spectrum is a steep function of temperature in the range of temperatures often encountered in research (e.g., between 100° C. and 1000° C.). Since NIR scenes change radiance dramatically with temperature, many applications require variations of exposure values by factors of 1000 or more, which may be difficult to obtain with electronic superframing alone.

Further, adding optical elements to an NIR system is not as difficult as in longer wavelength applications. For example, for an InSb or MCT (mercury cadmium telluride) camera operating in the 3-5 micron wavelength band, a room-temperature neutral density or bandpass filter can emit as much or more radiance onto the FPA as the scene radiance itself, so that the filter elements may need to be cooled to image the desired scene. By contrast, the NIR radiance of a blackbody at room temperature is extremely small, on the order of $10^{-7}$ compared to the radiance of a blackbody at 500K. Therefore, the optical elements in an NIR system need not be cooled below ambient temperature. This simplifies their use for many imaging scenarios.

Mechanical superframing provides additional benefits. For example, neutral density filters can yield extremely large changes in exposure. Filters with up to ND5 (transmission of $10^{-5}$) attenuation can be commercially obtained at relatively low cost. Additionally, the integration time used by the camera may be selected to be short, so that apparent motion within a single exposure is substantially frozen, to increase system frame rates. This is particularly beneficial in scenes with relatively high-speed motion, where blurring in the image may occur with longer integration times.

Figure 3A:
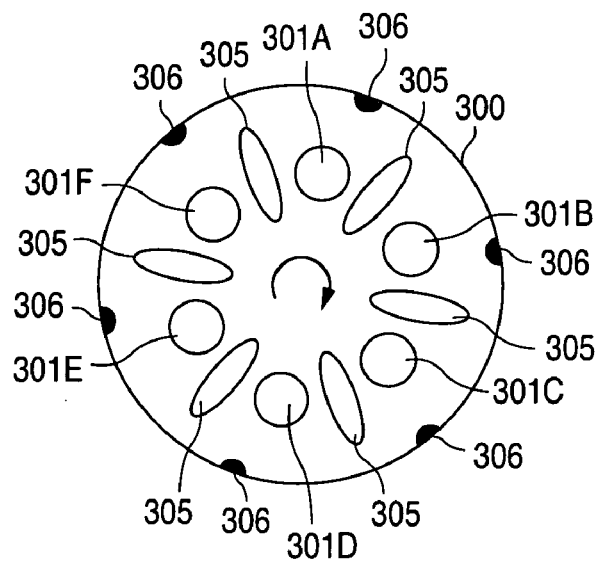
FIGS. 3A to 3C are schematic illustrations of filter holders that may be used for mechanical superframing, according to some embodiments.

FIG. 3A shows an embodiment of an apparatus for mechanical superframing. A filter support 300 is generally wheel-shaped, and includes a plurality of mounting features for holding an associated plurality of filters in different positions on filter support 300. The mounting features may include flanges that fix the filters in position on filter support 300.

In the illustrated example, filter support 300 holds six neutral density filters 301A to 301F. Neutral density filters are numbered according to the amount of light attenuated by the filter. An ND-0 filter transmits substantially all of the light incident on the filter, while an ND-1 filter transmits about 10% of the light incident on the filter, an ND-2 filter transmits about 1% of the incident light, and so on. In order to span a broad range of exposure levels, filters 301A to 301F may be ND-0 through ND-5 filters.

Filter support 300 is in communication with a motor (not shown) that spins filter support 300 rapidly about an axis into the page of FIG. 3A in the direction shown. As filter support 300 spins, each of the filters 301A to 301F are positioned in the optical path of the camera in turn. As a result, the exposure varies cyclically, from a maximum value (corresponding to the lowest filter level) to a minimum value (corresponding to the highest filter level).

Filter support 300 may include one or more cutouts 305 to decrease the moment of inertia about the rotation axis, to reduce gyroscopic effects that may occur when a camera including filter support 300 is rotated in pitch or yaw while the wheel is spinning. Filter support 300 may also include timing features 306 (e.g., notches) that may be used to generate a trigger for the camera to acquire image data for a particular filter 301.

The rotation frequency of filter support 300 may be selected to obtain the desired integration rate and frame rate. As the filter wheel speed is increased, the maximum superframe rate increases; however, the maximum integration time decreases proportionally. The rotation rate may thus be selected to obtain the best results for the particular application.

Figure 3B:
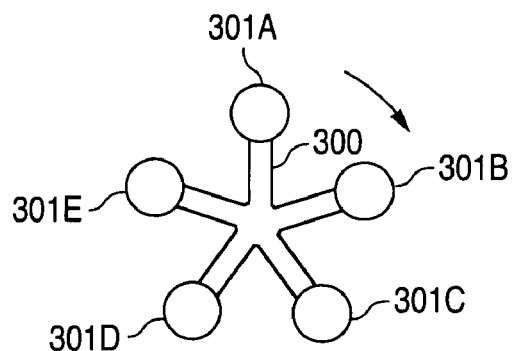
Figure 3C:
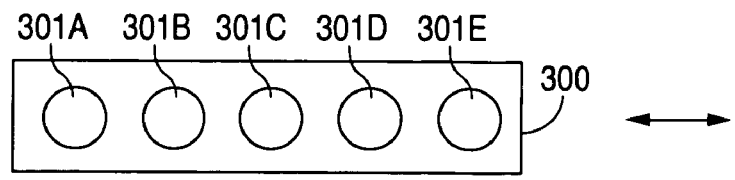

FIGS. 3B and 3C show different implementations of filter supports 300. In FIG. 3B, a spoke configuration is used rather than a wheel configuration. Each of the filters 301A to 301E are positioned in the optical path of the camera in turn. In FIG. 3C, a linear configuration of filters 301A to 301E is used. Rather than positioning the filters in the optical path cyclically, the filters may be positioned in the optical path in a forward order (e.g., 301A, 301B, 301C, 301D, and 301E), and then the reverse order (301E, 301D, 301C, 301B, 301A). Additionally, the time during which each filter is positioned in the optical path may differ for the embodiment of FIG. 3C.

Figure 4:
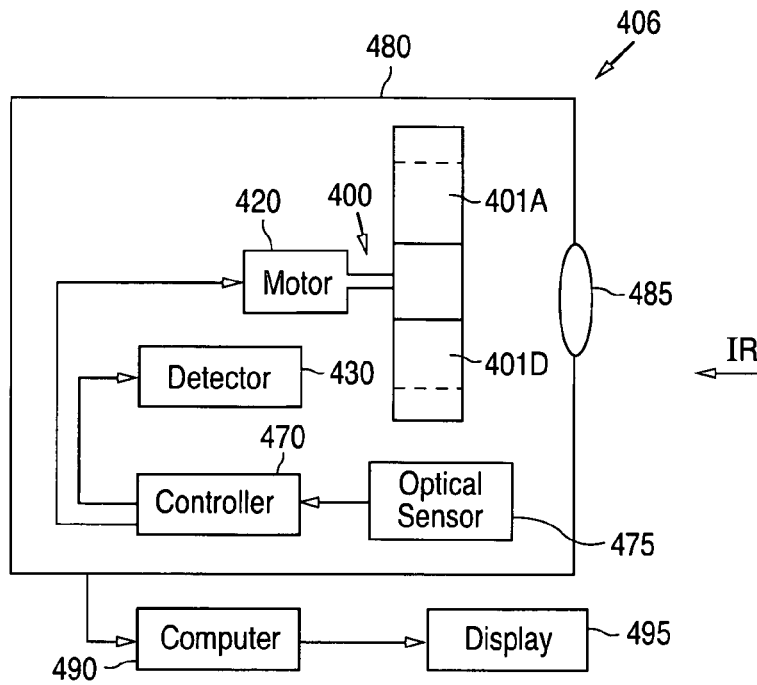
FIG. 4 is a schematic block diagram of a camera system, according to some embodiments.

FIG. 4 shows a schematic diagram of an infrared camera system 406 incorporating a filter holder 400 such as filter holder 300 of FIGS. 3A to 3C. Filter holder 400 includes a plurality of filters, including filter 401A and 401D. System 406 includes a camera unit 480 configured to receive infrared radiation through a lens 485 and to generate signals indicative of received radiation at a detector 430 such as a FPA detector.

Camera unit 480 further includes a motor 420 in communication with filter holder 400, which may be a calibrated stepper motor. In operation, motor 420 applies force (e.g., linear force and/or torque) to holder 400 to cause different filters of holder 400 to be positioned in the optical path of the infrared radiation, between lens 485 and detector 430. For example, motor 420 may apply torque to a wheel-shaped embodiment of a filter holder 400 to spin filter holder 400 at a pre-determined rotational frequency. Camera unit 480 further includes one or more controllers such as controller 470 to control one or more elements of system 406.

Camera unit 480 further includes a sensor 475 to sense the position of filter holder 400 and to generate a signal indicative thereof. For example, when filter holder 400 includes notches indicating the relative position of the filter holder, sensor 475 may detect light passing through one of the notches, and generate a signal to trigger detector 430 to acquire image data for a particular filter 401.

Infrared radiation incident on camera unit 480 through lens 485 is filtered by the filter positioned in the optical path of the IR radiation (in FIG. 4, filter 401D). In response to a signal from sensor 475, controller 470 generates a signal for detector 430 to acquire image data associated with the filter.

System 406 further includes one or more information processing systems configured to store and/or process data acquired by camera unit 480. As shown in FIG. 4, the information processing systems include a computer 490 external to camera unit 480, which is in turn in communication with an external display 495. However, at least some information processing functionality may be included in camera unit 480.

Figure 5:
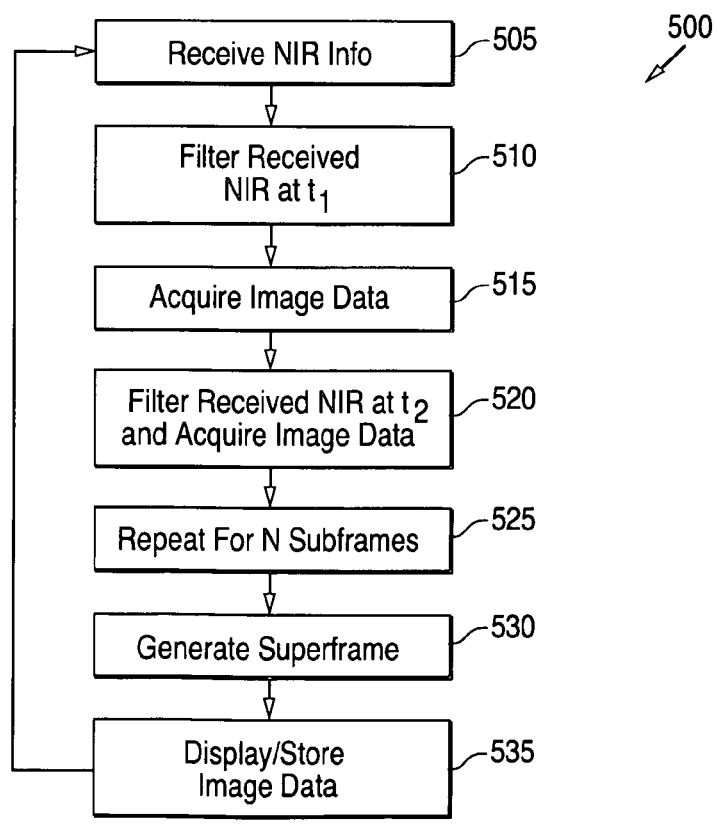
FIG. 5 is a method that may be used to generate one or more superframes using mechanical superframing techniques.

In operation, system 406 may obtain NIR images of an object or scene using a method such as method 500 illustrated in FIG. 5. At 505, NIR information is received from the object or scene. For example, NIR light radiated by the object or scene is received in system 406 via lens 485.

At 510, received NIR light is filtered with a first filter at $t_1$. For example, when a wheel-shaped filter holder is used, a motor applies torque to the filter holder to spin it at a high rate. At $t_1$, a first filter positioned in the filter holder is positioned in the optical path of the NIR received from the object or scene of interest.

At $t_1$, a plurality of detector elements of a detector array acquire image data for a first subframe $I_1$ associated with the first filter, at 515. The image data may be acquired using an integration time $\tau_1$ (at 515). The integration time is about equal to or less than a time during which the first filter is positioned in the optical path of the received NIR radiation (e.g., a time equal to or less than an effective width of the first filter divided by the speed of the filter wheel at the position of the first filter).

Similarly, at 520, received NIR light is filtered at a later time $t_2$ during which a second filter is positioned in the optical path of the received NIR radiation, and image data for a second subframe $I_2$ associated with the second filter is acquired (again, with an integration time $\tau_1$). At 525, NIR is filtered and image data is acquired for additional subframes associated with any additional filters. At 530, a superframe may be generated using images $I_1$ to $I_N$; for example, using the techniques described above for electronic superframing. At 535, image data associated with the generated superframe may be displayed and/or stored.

Method 500 may be used to generate a single image (one superframe) of the object or scene of interest, or may be repeated to generate a series of images (multiple superframes), to be displayed and/or stored. When multiple superframes are generated, they may be displayed and/or stored as video, so that changes of the object or scene over time may be displayed, analyzed, etc. For example, the superframe information may be used to make radiometric measurements, so that in-band radiance of targets may be measured.

As noted above, mechanical superframing may be accomplished using commercially available components. For example, commercial IR ND filters may be used. A common commercial ND filter is 1" in diameter. For some embodiments, filters can be mounted between the sensor and the camera lens without vignetting, since the ray cone coming out of most lenses is smaller than the clear aperture of 1" filters.

For embodiments in which no attenuation of the IR is needed for some subframes, an open space may be left in the filter holder, or a filter such as an ND 0.03 filter may be used. In some circumstances, it is better to use a filter than to leave an open space. For example, in order to keep the back working distance of the lens unchanged, the optical thickness of the filters should be substantially equal. In order to keep the optical thickness substantially constant, filters with glass substrates and metallic coatings may be used. The metallic coating reduces the transmitted light signal, but has a negligible effect on the optical thickness of the filters, since the coating is a small fraction of the total filter thickness. For the case where filters with thicknesses up to 3 mm are used, the current inventors have determined that the back working distance of standard C-mount color video lenses is substantially unchanged at high f/numbers.

The filter choice and other system configuration parameters may place limits on operational characteristics such as the integration time. For example, in an embodiment in which a filter wheel holds 1" diameter filters with a clear aperture of about 0.9 inches (where the aperture is reduced by flanges holding the filters in place), the current inventors measured an 11 degree range of rotation of the wheel between positions where the filter is not occluding the FPA. At a 15 Hz rotation rate, the duration of an 11 degree rotation is 2.14 msec, based on a calculated angular velocity of the wheel at 15 Hz of 5400 degrees/sec. The integration time for the above system configuration parameters thus limit the integration time to about 2.14 msec or less. For longer integration time operation, the angular speed of the wheel may be decreased. However, as noted above, increasing the maximum integration time reduces the attainable frame rate.

The following describes an embodiment that may be used to implement the systems and techniques described above. An IR camera system may include a commercial camera head, such as a FLIR Systems Phoenix NIR camera head with a 320×256 pixel array. The head may be connected to an RTIE unit (Real-time Imaging Electronics). The RTIE converts the raw FPA data into digital image data in the RS-422 standard format. The image data is transmitted to a National Instruments PCI-1422 frame grabber in the host computer.

For the described embodiment, the metal housing of a standard Phoenix head was replaced with an aluminum box which supports the filter holder between the lens interface and the sensor package. The lens interface was a standard C-mount thread cut into the front plate of the housing. An Animatics Smartmotor was used to rotate the filter wheel via a toothed-belt drive. The wheel's rotation was measured by an Omron position sensor that uses an infrared LED and phototransistor to detect the presence of small slots in the wheel (one slot per filter in this embodiment). A LabVIEW virtual instrument (VI) written by one of the inventors running on the host computer controlled the wheel speed, and detected the one-per-filter trigger signals generated by the Omron sensor. The VI generated a series of pulses timed off the Omron sensor, and these pulses were conditioned into rising-edge TTL level triggers with an adjustable phase delay that were fed to the external sync input of the RTIE connected to the Phoenix head.

The above example is one particular embodiment of the systems and techniques for mechanical superframing that may be used. Many others are possible. For example, different types of filters may be used, and the filter holder may position more than one type of filter in the optical path of the received IR radiation.

In addition, in some embodiments, multiple techniques for modifying the incoming light to image and/or analyze IR light from an object or scene may be used. For example, a single superframe may be generated using a plurality of subframes acquired using a first technique to modify the exposure (such as electronic superframing), and a plurality of subframes acquired using a second technique to modify the exposure (such as mechanical superframing). A superframe using two different exposure modification techniques may be referred to as a "hyperframe."

Figure 6A:
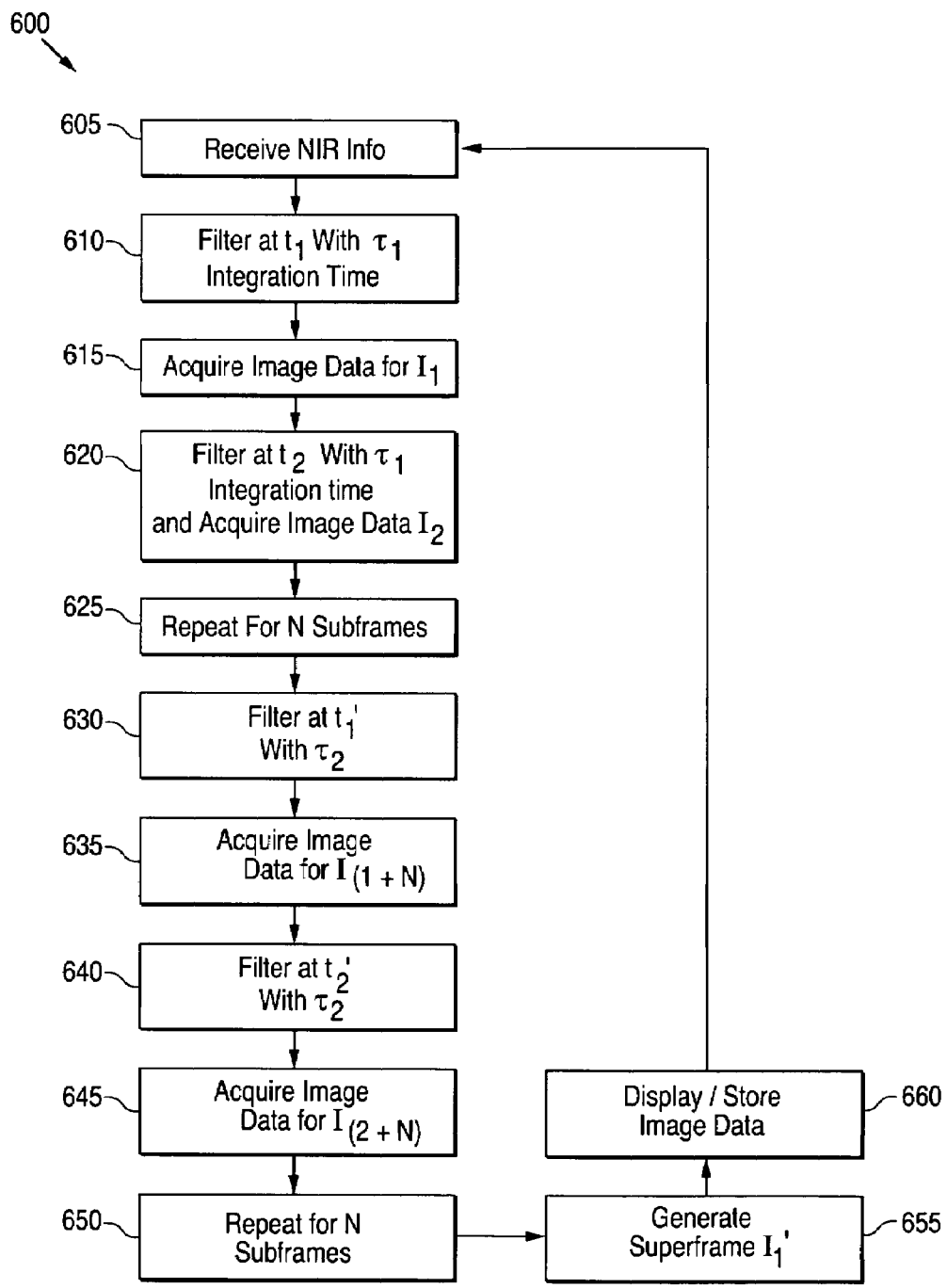
FIG. 6A is a method that may be used to generate one or more superframes using electronic and mechanical superframing techniques.
Figure 6B:
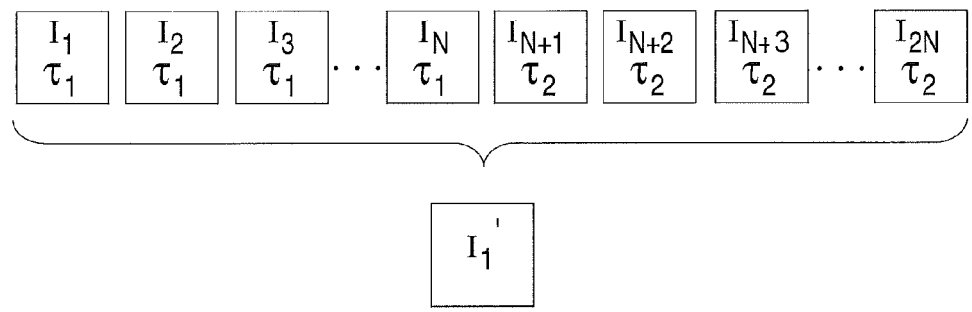
FIG. 6B shows 2N subframes and an associated superframe that may be generated using electronic and mechanical superframing techniques.

FIG. 6A shows an example of a method 600 incorporating both electronic and mechanical superframing techniques, while FIG. 6B shows an example of the acquired subframes and an associated superframe. Again, NIR imaging is used as an example, since self-emission of radiation of the filters in the NIR regime is negligible. Imaging in other regions of the spectrum (such as thermal IR) may also be performed. However, additional techniques may need to be used for other spectral regions; for example, the filters may need to be cooled to obtain a satisfactory signal to noise ratio.

At 605, NIR information is received at a camera system such as that shown in FIG. 4, which includes a filter holder to position N filters in the optical path of incoming IR radiation. At 610, incoming NIR light is filtered at a time $t_1$. At 615, subframe data for a first subframe $I_1$ associated with a first filter is acquired using an integration time $\tau_1$. At 620, incoming NIR light is filtered at a later time $t_2$, and subframe data is acquired for a second subframe $I_2$ associated with a second filter, using integration time $\tau_1$. At 625, the procedure is repeated for each of the N filters, to acquire image data for N subframes.

At 630, the first filter is again positioned in the optical path of incoming IR radiation at $t_1'$ (which may be substantially equal to $t_1+T$, where T is the rotation period of the filter wheel). At 635, image data for a subframe image $I_{(N+1)}$ may be acquired with an integration time $\tau_2$ different than $\tau_1$. At 640, incoming NIR is filtered with the second filter at a later time $t_2'$, and subframe data is acquired for a subframe $I_{(N+2)}$ associated with the second filter at 645, again with integration time $\tau_2$. At 650, the procedure is repeated until subframe data for N subframes is acquired with integration time $\tau_2$.

At 655, image information for a first superframe $I_1'$ is generated using subframe data for at least one of the subframes $I_1$ to $I_{(N+2)}$, as described above. At 660, the image information for first superframe $I_1'$ may be displayed and/or stored, and the procedure may be concluded, or may be repeated to acquire additional image information for additional superframes.

FIG. 6B shows the 2N subframes obtained using both electronic and mechanical superframe techniques. In order to generate image data for superframe $I_1'$ associated with the 2N subframes, the camera system may determine the best image data for each image pixel in superframe $I_1'$ from the associated pixel data in the 2N subframes, as described above.

Methods such as method 600 of FIG. 6A may provide for an extended dynamic range, while also providing additional flexibility. For example, the camera system need not use both electronic and mechanical superframing techniques in all circumstances. In some embodiments, the camera system may be configured to determine whether mechanical or electronic superframing alone may be sufficient to generate image data with the desired dynamic range and resolution. If it is, the system may select one technique or the other, and acquire superframes with a higher frame rate than when both techniques are used. However, if the system determines that the image data will not be sufficient using a single subframe acquisition technique, the system may implement multiple techniques for acquiring subframe data.

The systems and techniques described herein may be applied in a number of ways. For example, image data may be obtained and displayed and/or analyzed to determine the thermal properties of the imaged object or scene. Additionally, the techniques may be used to perform thermography for one or more graybodies in a scene being imaged. For example, by incorporating different types of filters in one or more filter holders such as those illustrated in FIGS. 3A to 3C, properties such as the radiance or temperature of a graybody may be determined, without knowing the emissivity of the graybody.

Most physical objects emit infrared radiation as graybodies; that is, most objects have an emissivity of less than one. By contrast, a blackbody has an emissivity of one, and for a temperature T emits radiation according to Planck's blackbody equation:

$$W(\lambda) = \frac{2\pi hc^2}{\lambda^5} \frac{1}{\left(e^{\frac{hc}{\lambda kT}} - 1\right)}$$

Figure 7:
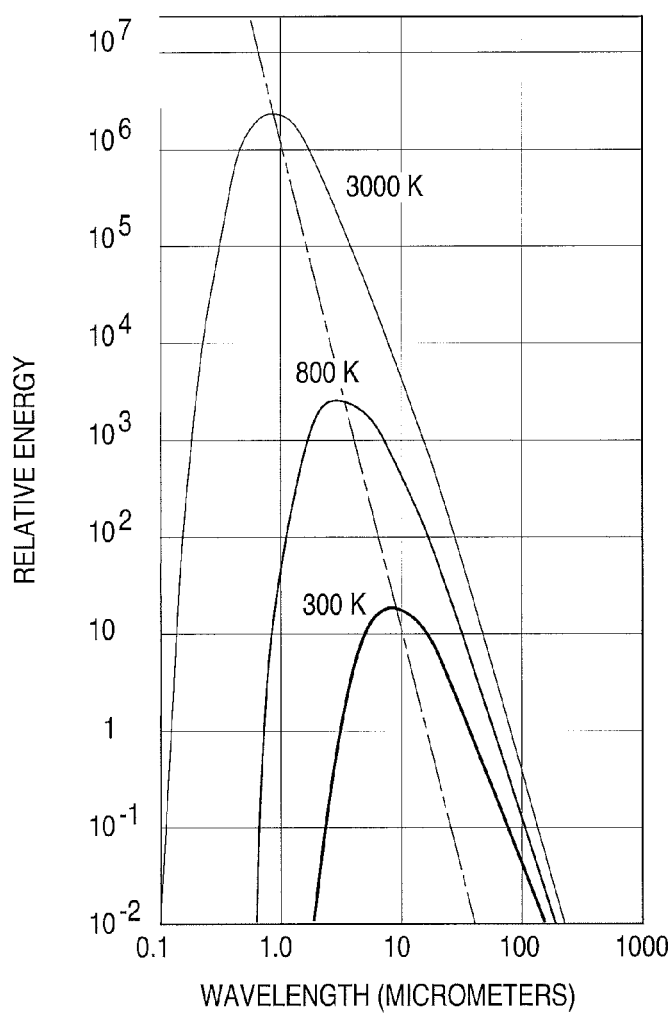
FIG. 7 illustrates the spectral radiant emittance equation at three different temperatures.

Usually, in order to determine properties of a graybody by detecting emitted IR radiation, its emissivity needs to be known. FIG. 7 shows blackbody curves for a blackbody at 300K, 800K, and 3000K. The curves for graybodies are shifted by the emissivity of the body, which is sometimes a substantially constant function of wavelength. Thus, while measurement of the radiance of a blackbody at a particular wavelength yields the blackbody's temperature, it is insufficient to determine the temperature of a graybody (unless the emissivity is also known).

Figures 8, 9B:
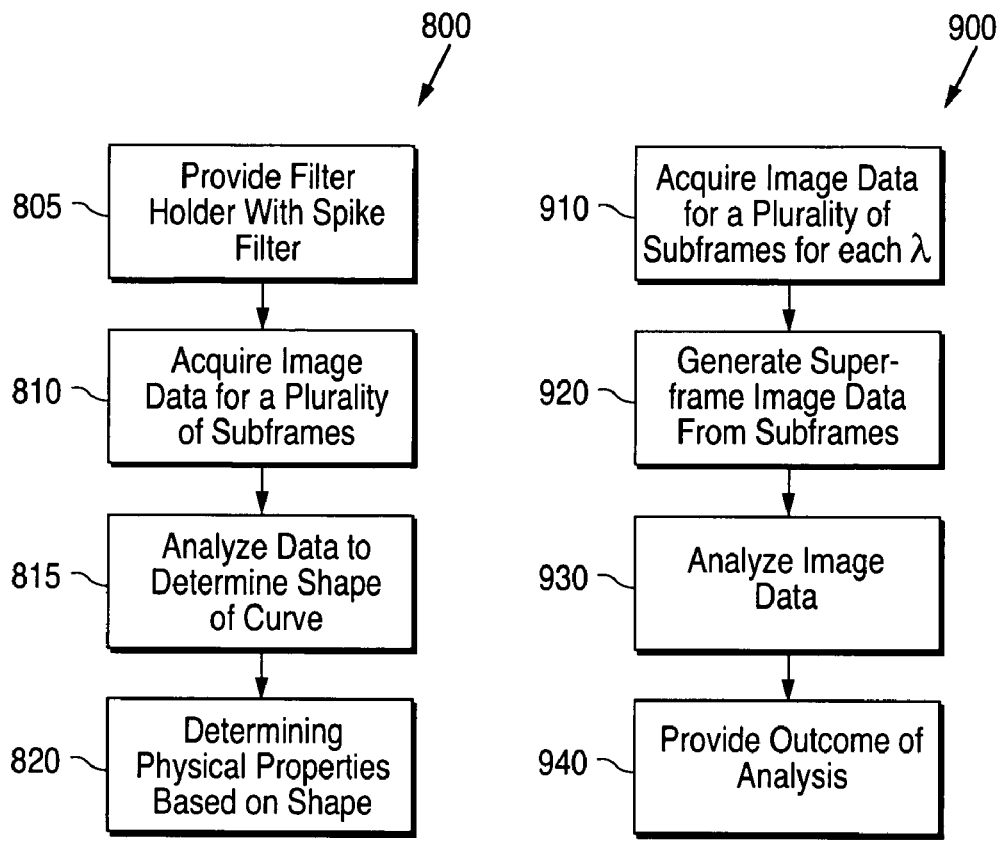
FIG. 8 shows a method that may be used to determine physical properties of a graybody using superframing techniques.
FIG. 9B is a method that may be used for imaging spectroscopy using electromagnetic signature information, according to some embodiments.

However, FIG. 8 shows a method 800 that may be used with a camera system such as system 406 of FIG. 4 to determine properties such as the IR flux and/or graybody temperature without knowing the emissivity. At 805, a filter holder with spike filters corresponding to at least two wavelengths in the expected graybody spectrum is provided. A spike filter is a type of bandpass filter that passes a narrow wavelength band. In one example, spike filters for various wavelengths between 0.9 microns and 1.7 microns may be provided. The camera system may be calibrated with the spike filters installed in the filter holder by acquiring data from a blackbody at one or more known temperatures, so that the radiance for a particular detector signal is known prior to obtaining image data for a graybody of interest.

At 810, image data may be acquired for a plurality of subframes. This may be accomplished using the systems and techniques described above. For example, in one embodiment, each of the spike filters may be positioned in turn in the optical path of the IR for a first integration time (to obtain first subframe data at each wavelength), then for a second integration time (to obtain second subframe data at each wavelength), and so on.

In another embodiment, spike filters may be used in addition to ND filters, where the spike filters allow the acquisition of image data at particular wavelengths and the ND filters allow the exposure to be altered to increase the dynamic range of the image data acquisition. For example, a first filter holder may include a plurality of spike filters corresponding to the wavelengths of interest. A second filter holder may include a plurality of ND filters to obtain data within a particular dynamic range. Image data for a first wavelength may be obtained by placing the desired spike filter in the optical path of the IR, and positioning each of the ND filters in the optical path in turn. The resulting subframes may be combined to generate image information for a superframe associated with the first wavelength. The procedure may be repeated for each of the spike filters.

At 815, the acquired image data may be analyzed to determine the shape of the graybody curve. At 820, the desired physical properties may be determined based on the shape of the graybody curve. For example, the temperatures of a number of objects in a scene may be determined, without knowing the emissivity of the objects.

The systems and techniques described above may also be used for spectral imaging of scenes.

In a number of circumstances, it may be useful to analyze a scene to look for one or more particular object types or material types. For example, it may be useful to acquire image data of a large agricultural area, and to detect the presence of healthy or unhealthy crops. In order to discriminate among different image constituents, IR and/or near-IR signatures of objects of interest may be acquired and stored as a library for later comparison.

Figure 9A:
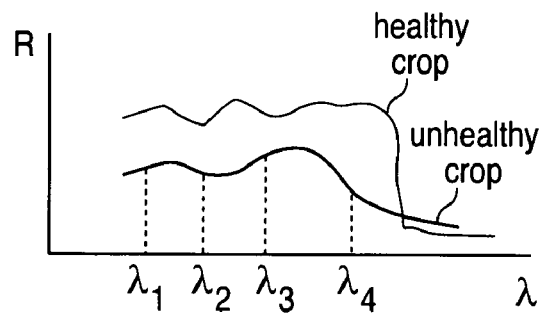
FIG. 9A illustrates electromagnetic signatures of a healthy crop and an unhealthy crop.

FIG. 9A shows hypothetical reflectance versus wavelength signatures of a healthy crop and an unhealthy crop. Spectral information for each of the crop types may be stored for later comparison to acquired image data. The spectral information may include information indicative of the reflectance as a function of wavelength, as shown in FIG. 9A.

In order to identify one or more constituents of a scene, image data of the scene may be acquired for a number of discrete wavelengths. For example, in FIG. 9A, four principle components of the spectrum are denoted as wavelengths 1, 2, 3, and 4. A spectral imaging system may include spike filters for various wavelengths of the spectral region of interest. For example, the imaging system may include spike filters for four wavelengths between 0.9 microns and 1.7 microns.

FIG. 9B shows a method 900 that may be used to perform imaging spectroscopy, using a camera system such as system 406 of FIG. 4. At 910, image data may be acquired for a plurality of subframes. This may be accomplished using the systems and techniques described above. For example, in one embodiment, each of the spike filters may be positioned in turn in the optical path of the IR for a first integration time (to obtain first subframe data at each wavelength), then for a second integration time (to obtain second subframe data at each wavelength), and so on.

In another embodiment, spike filters may be used in addition to ND filters, where the spike filters allow the acquisition of image data at particular wavelengths and the ND filters allow the exposure to be altered to increase the dynamic range of the image data acquisition. For example, a first filter holder may include a plurality of spike filters corresponding to the wavelengths of interest. A second filter holder may include a plurality of ND filters to obtain data within a particular dynamic range. Image data for a first wavelength may be obtained by placing the desired spike filter in the optical path of the IR, and positioning each of the ND filters in the optical path in turn. At 920, the resulting subframes may be combined to generate image information for a superframe associated with the first wavelength. The procedure may be repeated for each of the spike filters.

At 930, the acquired image data may be analyzed by comparing the image data to reference spectroscopic data. For example, the image data may be analyzed to determine the presence or absence of one or more particular materials in the image, or to identify particular image constituents. In order to determine the presence of one or more particular materials in the image, the image data may be compared to stored spectrographic information for the particular constituents. In order to identify particular image constituents, the image data may be compared to stored spectrographic information for a number of different materials.

For example, in order to determine the presence of unhealthy crop materials in a region represented by the image data, the spectrographic information for each pixel of the image data may be compared to stored spectrographic information for the unhealthy crop materials. The image information may thus be used to determine whether a particular disease has affected an agricultural region and, if so, the extent of the damage.

In another example, the acquired image data may be analyzed to determine the percentage of the imaged region corresponding to green space or to asphalt. The results of the analysis may then be used to improve urban planning.

At 940, the outcome of the analysis may be provided via a display or other output. For example, an image may be generated in which particular constituents (such as unhealthy crops) are presented in a first color, displayed with a border indicating regions including the particular constituents, or in another manner.

In implementations, the above described techniques and their variations may be implemented at least partially as computer software instructions. Such instructions may be stored on one or more machine-readable storage media or devices and are executed by, e.g., one or more computer processors, or cause the machine, to perform the described functions and operations.

A number of implementations have been described. Although only a few implementations have been disclosed in detail above, other modifications are possible, and this disclosure is intended to cover all such modifications, and most particularly, any modification which might be predictable to a person having ordinary skill in the art. For example, although some techniques may be particularly beneficial for NIR imaging, they need not be restricted to that portion of the electromagnetic spectrum. Additionally, the phrases "image data" and "image information" refer to data/information based on received electromagnetic radiation from one or more objects, and need not be used to generate an image (e.g., it may be used for radiance information with or without generating an actual image).

Also, only those claims which use the word "means" are intended to be interpreted under 35 USC 112, sixth paragraph. Moreover, no limitations from the specification are intended to be read into any claims, unless those limitations are expressly included in the claims. Accordingly, other embodiments are within the scope of the following claims.

What is claimed is:

1. An article comprising a computer-readable storage medium embodying information indicative of instructions that when performed by one or more computers result in operations comprising:
   positioning a first filter in the optical path of an infrared camera, the first filter configured to pass a narrow wavelength band including a first wavelength;
   acquiring first subframe image data associated with the first wavelength at a detector using a first exposure;
   acquiring second subframe image data associated with the first wavelength at the detector using a second exposure;
   generating first wavelength image data based on at least some of the first subframe image data and the second subframe image data;
   positioning a second filter in the optical path of the infrared camera, the second filter configured to pass a narrow wavelength band including a second different wavelength;
   acquiring image data associated with the second wavelength at the detector;
   generating second wavelength image data based on the image data associated with the second wavelength; and
   comparing the first wavelength image data and the second wavelength image data to reference spectroscopic data.

2. The article of claim 1, further comprising determining the presence or absence of a particular material corresponding to the reference spectroscopic data.

3. The article of claim 1, wherein the first wavelength image data comprises image data corresponding to a plurality of pixels of the image, and wherein comparing the first wavelength image data to reference spectroscopic data comprises comparing first wavelength data for each of the plurality of pixels to the reference spectroscopic data.

4. The article of claim 1, wherein acquiring the first subframe image data associated with the first wavelength at the detector using the first exposure comprises acquiring the first subframe image data at a first integration time, and wherein acquiring the second subframe image data associated with the first wavelength at the detector using the second exposure comprises acquiring the first subframe image data at a second different integration time.

5. The article of claim 1, wherein acquiring the first subframe image data associated with the first wavelength at the detector using the first exposure comprises acquiring the first subframe image data using a first filter with a first attenuation, and wherein acquiring the second subframe image data associated with the first wavelength at the detector using the second exposure comprises acquiring the first subframe image data using a second filter with a second different attenuation.

6. The article of claim 1, wherein comparing the first wavelength image data and the second wavelength image data to reference spectroscopic data comprises comparing the first wavelength image data and the second wavelength image data to reference spectroscopic data corresponding to a plurality of different materials.

7. The article of claim 6, wherein the first wavelength image data comprises image data corresponding to a plurality of pixels of the image, and wherein comparing the first wavelength image data to reference spectroscopic data corresponding to the plurality of different materials comprises comparing first wavelength data for each of the plurality of pixels to the reference spectroscopic data for at least one of the different materials.

8. A method comprising:
   positioning a first filter in the optical path of an infrared camera, the first filter configured to pass a narrow wavelength band including a first wavelength;
   acquiring first subframe image data associated with the first wavelength at a detector using a first exposure;
   acquiring second subframe image data associated with the first wavelength at the detector using a second exposure;
   generating first wavelength image data based on at least some of the first subframe image data and the second subframe image data;
   positioning a second filter in the optical path of the infrared camera, the second filter configured to pass a narrow wavelength band including a second different wavelength;
   acquiring image data associated with the second wavelength at the detector;
   generating second wavelength image data based on the image data associated with the second wavelength; and
   comparing the first wavelength image data and the second wavelength image data to reference spectroscopic data.

9. The method of claim 8, further comprising determining the presence or absence of a particular material corresponding to the reference spectroscopic data.

10. The method of claim 8, wherein the first wavelength image data comprises image data corresponding to a plurality of pixels of the image, and wherein comparing the first wavelength image data to reference spectroscopic data comprises comparing first wavelength data for each of the plurality of pixels to the reference spectroscopic data.

11. The method of claim 8, wherein acquiring the first subframe image data associated with the first wavelength at the detector using the first exposure comprises acquiring the first subframe image data at a first integration time, and wherein acquiring the second subframe image data associated with the first wavelength at the detector using the second exposure comprises acquiring the first subframe image data at a second different integration time.

12. The method of claim 8, wherein acquiring the first subframe image data associated with the first wavelength at the detector using the first exposure comprises acquiring the first subframe image data using a first filter with a first attenuation, and wherein acquiring the second subframe image data associated with the first wavelength at the detector using the second exposure comprises acquiring the first subframe image data using a second filter with a second different attenuation.

13. The method of claim 8, wherein comparing the first wavelength image data and the second wavelength image data to reference spectroscopic data comprises comparing the first wavelength image data and the second wavelength image data to reference spectroscopic data corresponding to a plurality of different materials.

14. The method of claim 13, wherein the first wavelength image data comprises image data corresponding to a plurality of pixels of the image, and wherein comparing the first wavelength image data to reference spectroscopic data corresponding to the plurality of different materials comprises comparing first wavelength data for each of the plurality of pixels to the reference spectroscopic data for at least one of the different materials.

15. An infrared camera system comprising:
- a filter holder configured to hold a first spike filter associated with a first wavelength and a second spike filter associated with a second wavelength, the filter holder further configured to position the first spike filter in the optical path of the infrared camera system for a first time interval and to position the second spike filter in the optical path of the infrared camera system for a second time interval;
- a detection system configured to receive light from the first spike filter at a first exposure and to generate first subframe information indicative thereof, the detection system further configured to receive light from the first spike filter at a second exposure and to generate second subframe information indicative thereof, the detection system configured to receive light from the second spike filter at the first exposure and to generate third subframe information indicative thereof, the detection system further configured to receive light from the second spike filter at the second exposure and to generate fourth subframe information indicative thereof; and
- a processor configured to receive the first subframe information and the second subframe information and to generate first superframe information associated with the first wavelength based on at least a part of the first subframe information and the second subframe information, the processor further configured to receive the third subframe information and the fourth subframe information and to generate second superframe information associated with the second wavelength based on at least a part of the third subframe information and the fourth subframe information, the processor further configured to compare the first superframe information and the second superframe information to reference spectroscopic data.

16. The system of claim 15, wherein the infrared camera comprises a near-infrared (NIR) camera.

17. The system of claim 15, further comprising a second filter holder configured to position a first filter in the optical path of the infrared camera system for the first exposure and to position a second different filter in the optical path of the infrared camera system for the second exposure.

18. The system of claim 15, wherein the processor is further configured to determine the presence or absence of a particular material corresponding to the reference spectroscopic data.

19. The system of claim 15, wherein the first superframe information comprises a first superframe information corresponding to a plurality of image pixels, and wherein comparing the first superframe information to reference spectroscopic information comprises comparing the first superframe information for each of the plurality of image pixels to the reference spectroscopic information.

20. The system of claim 15, wherein comparing the first superframe information and the second superframe information to reference spectroscopic data comprises comparing the first wavelength image data and the second wavelength image data to reference spectroscopic data corresponding to a plurality of different materials.

* * * * *